United States Patent

Kalopissis et al.

[11] 3,957,774
[45] May 18, 1976

[54] N-MORPHOLINOMETHYL-N-'-SUBSTITUTED ETHYL AND PROPYLUREAS

[75] Inventors: Gregoire Kalopissis, Paris; Jean-Louis Abegg, Le Perreux; Guiliana Ghilardi; Henri Philippe de Beaulieu, both of Paris, all of France

[73] Assignee: L'Oreal, Paris, France

[22] Filed: Feb. 6, 1975

[21] Appl. No.: 547,394

Related U.S. Application Data

[60] Division of Ser. No. 244,906, April 17, 1972, Pat. No. 3,882,114, and a continuation-in-part of Ser. No. 770,074, Oct. 23, 1968, Pat. No. 3,678,157.

[52] U.S. Cl. ............... 260/246 B; 8/127.51; 8/127.6; 260/247.1 R; 260/247.2 A; 260/268 R; 260/268 H; 260/293.7; 260/293.85; 260/293.86; 260/309.7; 260/552 R; 260/553 R; 424/248; 424/72; 424/70; 424/71

[51] Int. Cl.² ............ C07D 295/12; C07D 295/14

[58] Field of Search ............... 260/246 B, 247.1 R, 260/247.2 A

[56] References Cited
UNITED STATES PATENTS

| | | | |
|---|---|---|---|
| 3,678,157 | 7/1972 | Kalopissis et al. | 424/71 |
| 3,882,114 | 5/1975 | Kalopissis et al. | 260/247.1 R |

*Primary Examiner*—Alton D. Rollins
*Assistant Examiner*—Jose Tovar
*Attorney, Agent, or Firm*—Cushman, Darby & Cushman

[57] ABSTRACT

Polycondensable compound and a process for treating hair employing a composition containing said polycondensable compound having the formula

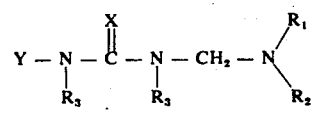

wherein X is O or S; $R_1$ and $R_2$ are ethyl or together form the divalent radical —$CH_2$—$CH_2$—O—$CH_2$—$CH_2$—, —$CH_2$—$CH_2$—$CH_2$—$CH_2$—$CH_2$— or

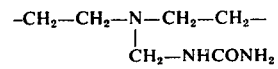

$R_3$ and $R_3'$ are hydrogen or taken together form the divalent radical —$CH_2$—$CH_2$—, Y is hydrogen,

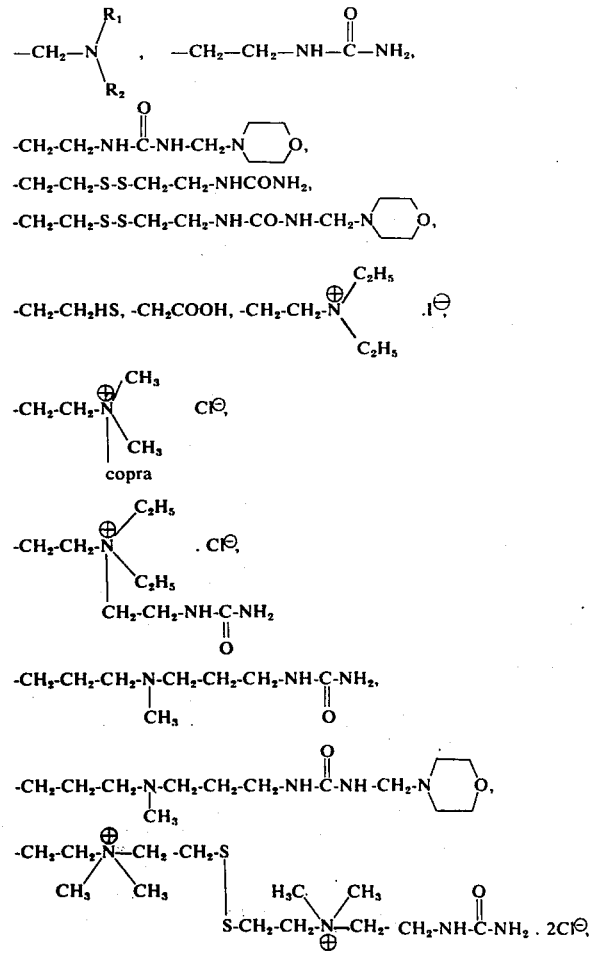

—$C_{12}H_{25}$ and —$C_{18}H_{37}$ and an acid catalyst in an amount effective to polymerize the compound on the hair and then drying the hair.

2 Claims, No Drawings

N-MORPHOLINOMETHYL-N-'-SUBSTITUTED ETHYL AND PROPYLUREAS

This is a division of application Ser. No. 244,906 filed Apr. 17, 1972 now U.S. Pat. No. 3,882,114, issued 5-6-1975 and a continuation-in-part of our earlier application Ser. No. 770,074, filed Oct. 23, 1968 now Pat. No. 3,678,157, issued July 18, 1972.

This invention relates to a cosmetic composition for improving the condition of human hair and imparting thereto properties which are advantageous when the hair is to be subsequently subjected to a cosmetic treatment.

It is known that the hair is more or less degraded by the action of atmospheric agents such as the sun and sea water, and by chemical treatments to which they are subjected, for example, during permanent waving and bleaching.

The effects of such degradation may be to a large extent eliminated by using the compositions according to the present invention.

It has already been proposed to increase the strength and elasticity of the hair by treating it with compounds which can be polymerized inside the keratin fiber, and at the same time become attached to the reactive groups of the keratin.

Among the compounds heretofore suggested for this purpose are dimethylolurea and dimethylolthiourea, which have, however, the disadvantage of causing the release of a substantial quantity of free formol, the presence of which in contact with the scalp cannot be tolerated.

It has also been suggested to use for this same purpose compounds which are more stable than dimethylolurea and dimethylolthiourea, that is to say, compounds which release much less free formol.

However, these compounds exhibit the common characteristic of having hydroxymethyl group substituents which prevent them from being completely stable. Moreover, these products are difficult to prepare in a very pure state and consequently the process for preparing them does not lead to rigorously reproducible results.

Furthermore, a great many of these compounds are difficult to dissolve in aqueous solvents which are generally used in the cosmetic field.

In order to at least partially eliminate these disadvantages, it has been suggested that one use, instead of the hydroxymethyl derivatives themselves, particular derivatives of these compounds obtained in a known manner by condensing them with secondary amines in accordance with the Mannich reaction.

The compounds produced in accordance with this reaction are more soluble, more stable, and easier to prepare than the corresponding hydroxymethyl compounds and are thus appreciably more satisfactory when used for the cosmetic purpose of strengthening the hair.

Specifically, cosmetic compounds having disulfide bonds have been chemically attached to the hair. This supplement to the S—S bonds improves the behavior of the hair and affects the action of the fiber with respect to the chemical reactants customarily used in the cosmetic field, such as reducing solutions containing mercaptans or sulfites, or oxidizing agents containing hydrogen peroxide, for example.

In like manner cosmetic compounds having carboxylic groups have been attached inside the hair. These additional acid groups greatly increase the affinity of the fiber for basic dyes.

On the other hand, basic groups, or even fatty chains, have been introduced into the hair in order to increase the affinity of the hair for acid dyes, or improve the sheen and "feel" of the hair over a substantial period of time.

It has now been discovered that these different purposes can be served by using compounds having in their molecule both a function capable of causing polycondensation and a function serving the other cosmetic purposes outlined above. In this manner, when this type of product is polycondensed in a conventional manner inside the keratin, the result is to achieve simultaneously both the desired cosmetic effect and improved properties with respect to their mechanoelastic behavior.

It is therefore an object of the present invention to provide a process for treating or modifying the keratin of the hair comprising applying to the hair an effective amount of a composition containing in a solvent selected from the group consisting of water and an aqueous alcoholic solution 0.5–12 weight percent of a polycondensable compound having the formula:

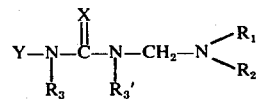

wherein X is selected from the group consisting of oxygen and sulfur;

$R_1$ and $R_2$ are selected from the group consisting of ethyl and, when taken together, a divalent radical selected from the group consisting of —CH$_2$—CH$_2$—O—CH$_2$—CH$_2$—, —CH$_2$—CH$_2$—CH$_2$—CH$_2$—CH$_2$—, and

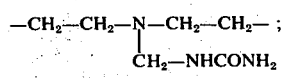

$R_3$ and $R'_3$ are selected from the group consisting of hydrogen and, when taken together, a divalent radical having the formula —CH$_2$—CH$_2$—; Y is selected from the group consisting of hydrogen,

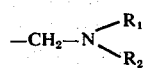

wherein $R_1$ and $R_2$ having the meaning given above,

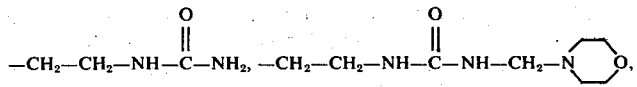

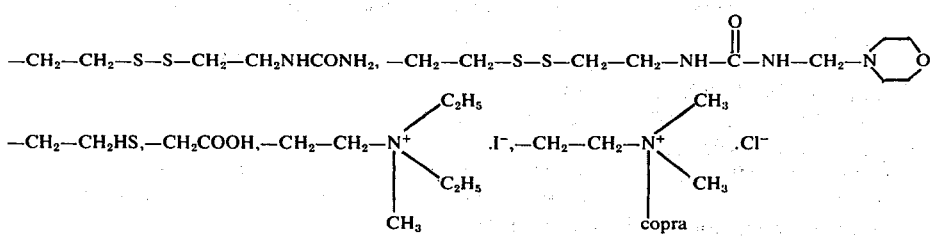

wherein copra is a mixture of alkyl and alkenyl having 6–18

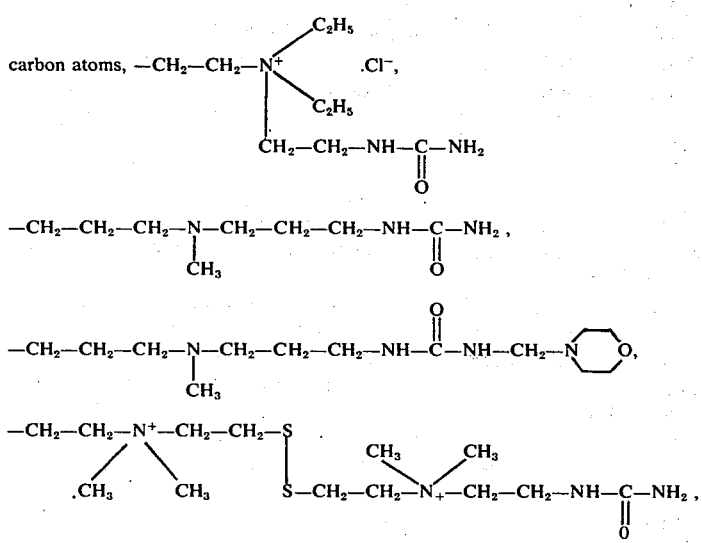

carbon atoms,

—$C_{12}H_{25}$ and —$C_{18}H_{37}$.

The solvent, as stated, can be water or an aqueous alcoholic solution and when the latter is chosen the alcohol generally employed is either ethanol or isopropanol present in amounts up to about 70 percent by weight of said aqueous alcoholic solution.

In combination with said polycondensable compound there is employed an acid catalyst in amounts effective to polymerize said compound on the hair. Thereafter, the hair is dried.

Representative of such polycondensable compounds are monomorpholinomethylurea, dimorpholinomethylurea, dimorpholinomethylthiourea, monomorpholinomethylthiourea, monomorpholinomethylethyleneurea, 1,4-bis(carbamidomethyl) piperazine, diethylaminomethylurea, monomorpholinomethylethylene diurea, dimorpholinomethylene diurea, piperidinomethylurea, (N-carbamyl-N'-morpholinomethylcarbamyl)cystamine, N,N'-(morpholinomethylcarbamyl)cystamine, N-(morpholinomethylcarbamyl)cysteamine, N-(moropholinomethylcarbamyl) glycine, (diethylmethylmorpholinomethyl ureidoethyl)ammonium iodide, (dimethylcopra-morpholinomethyl ureidoethyl)ammonium chloride, [N-(morpholinomethyl)ethylurea diethyl ethylurea] ammonium chloride, methylpropylurea N-(morpholinomethyl) propylurea amine, methyl di-[N-(morpholinomethyl)propylurea amine], (N-dimethyl ethylurea-N40 -dimethyl morpholinomethyl ureidoethyl)cystamine dichloride, N-dodecyl, N'-(morpholinomethyl)urea and N-octadecyl, N'-(morpholinomethyl)urea.

Of particular interest in the present invention is the use of a polycondensable compound having the formula

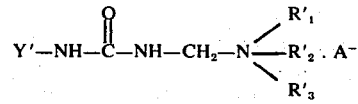

wherein Y' is selected from the group consisting of hydrogen and —$CH_2OCH_3$, $R'_1$ and $R'_2$ together represent a member selected from the group consisting of (1) a divalent radical having the formula —$CH_2$—$CH_2$—O—$CH_2$—$CH_2$, in which case $R'_3$ is methyl and (2) together with $R'_3$ represent a member having the formula —CH=CH—CH=CH—CH=, and A represents an anion selected from the group consisting of iodide and chloride.

Representative of such compounds are morpholinomethylurea quaternized with methyliodide and methoxymethylureidomethyl pyridinium chloride.

As the acid catalyst employed with the polycondensable compound in the process of the present invention the following are representative of those usefully employed: sulfuric, hydrochloric, phosphoric, citric, lactic, formic, acetic, p-toluenesulfonic, tartaric, succinic, glycolic, salicylic, oxalic, malic, phenylacetic and nicotinic acids. Particularly effective catalysts are sodium and potassium monophosphates.

The cosmetic composition utilized in the present invention generally has a pH ranging between 1 and 5 and ordinarily is applied to the hair in amounts of about 10–30 cc. It will be appreciated, however, that the amount of the composition applied to the hair can vary depending on, for instance, the amount of hair to be treated.

Further, the cosmetic compositions employed in the present invention can also contain one or more ureins, such as those having the following formula:

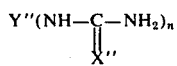

wherein X'' is selected from the group consisting of O, S and NH, n = 1 or 2 and Y'' is a chemical group which has cosmetic properties and is selected from the group consisting of disulfide, carboxylic acid, tertiary amine, quaternary amine, fatty chain and —SH groups.

The cosmetic composition employed in the present invention can be provided in the form of a gel, a cream, or an aerosol. It can also contain conventional cosmetic additives, such as surface-active agents, penetrating agents, perfumes, resins and the like.

Moreover, the cosmetic composition can be provided in the form of a two-package assembly, the contents of said packages designed to be mixed just prior to use on the hair. One of said packages contains the polycondensable compound in solid form while the other package contains the aqueous or aqueous alcoholic solvent together with the acid catalyst, as well as any conventional cosmetic additive desired to be included in the overall composition.

In particular, the solid or aqueous phase of the cosmetic composition packaged in this manner can also contain a salt of sulfurous acid, such as sodium metabisulfite.

A further object of the present invention is to provide a new process for treating hair characterized by the fact that the hair is impregnated with the above composition, and dried by the application of heat. If desired, the hair can be rinsed prior to drying the same.

In a first method of carrying out this process, the cosmetic composition does not itself contain the acid catalyst necessary to cause polycondensation of the polycondensable compounds in the keratinic fiber, and this acid catalyst is instead applied directly to the hair either before or after applying the cosmetic composition of this invention.

In another method of carrying out this process, a cosmetic composition which does contain the acid catalyst is applied directly to the hair, which is then dried as previously described.

The treatment according to the invention makes it possible to substantially strengthen the keratinic fiber of the hair by forming a polycondensate inside the hair which also becomes attached to the reactive groups of the keratin. This treatment makes it possible to obtain sets of excellent quality when the hair is treated while wound up on setting rollers.

On the other hand, when the polycondensable compounds also contain other cosmetic constituents, the treatment according to the invention also makes it possible to carry out subsequent cosmetic treatments, such as bleachings, dyeings, permanent wavings and the like under greatly improved conditions.

It is a further object of the present invention to provide as a new article of manufacture, a compound corresponding to the formula:

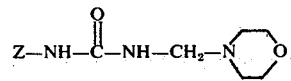

wherein Z is selected from the group consisting of:

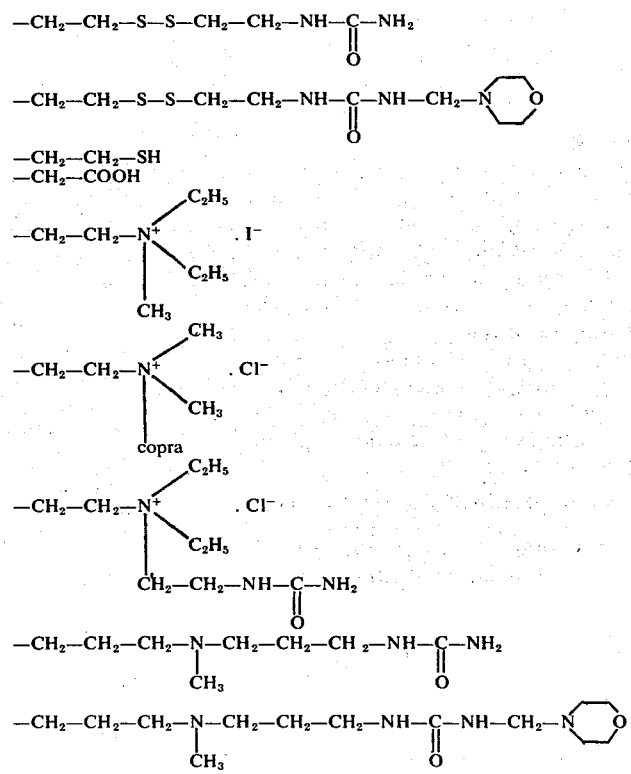

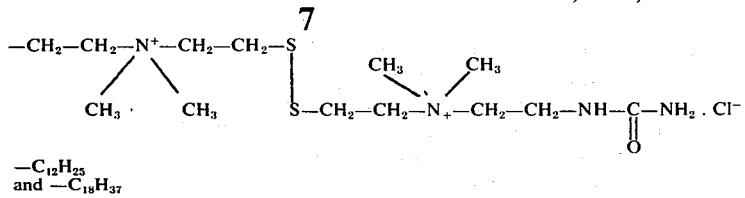

—$C_{12}H_{25}$
and —$C_{18}H_{37}$

Representative of such compounds are: (N-carbamyl N'-morpholinomethylcarbamyl)cysteamine; N,N'-(morpholinomethylcarbamyl)cysteamine; N-(morpholinomethylcarbamyl)cysteamine; N-(morpholinomethylcarbamyl)glycine; (diethyl methyl morpholinomethylureidoethyl)ammonium iodide; (dimethyl copra morpholinomethylureidoethyl)ammonium chloride; N-(morpholinomethyl)ethylurea-diethyl-ethylurea ammonium chloride; methyl-propylurea N-(morpholinomethyl)propylurea amine; methyl di-N-(morpholinomethyl)propylurea amine; (N-dimethyl ethylurea-N'-dimethyl morpholinomethylureidoethyl)cysteamine dichloride; N-dodecyl-N'-(morpholinomethyl)urea; and N-octadecyl N'-(morpholinomethyl)urea.

The above new compounds can be prepared in accordance with the following method:

In a first step, a urein of the following formula is prepared:

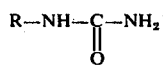 (I)

This type of compound is prepared by reacting an alkali cyanate (Na or K) with a primary amino hydrochloride according to the known process described in Organic Synthesis Vol. 3 - 1963 page 515.

The reaction scheme is:

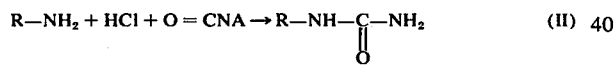 (II)

A = Na or K

In a second step, a reaction of Mannich type such as described in "Organic Reaction" Vol. I, Ch. 10, p. 303 and Houban Weyl XIV/2, p.342-354 is carried out by reacting the above Urein (II) which has thus been formed with a secondary amine (in the present case with morpholine) in the presence of formol in stoichiometric quantity or in slight excess.

The reaction is carried out in aqueous solution either at room temperature or at a temperature of about 20°C to 60°C. In some cases the reaction is exothermic.

The yield of the Mannich reaction is generally comprised between 80 and 100%.

EXAMPLES OF PREPARATION

Example 1 - Preparation of dimorpholinomethylthiourea

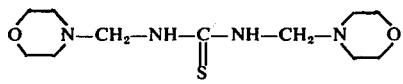

1 mol of thiourea is dissolved in two mols of formol in an aqueous 30% solution, at a temperature of 40°–50°C.

This mixture is cooled below 20°C and 2 mols of morpholine are added slowly while keeping the temperature between 15° and 20°C. This resulting mixture is then cooled to −10°C until the dimorpholinomethyl thiourea crystallizes out, which takes at least 24 hours.

The resulting product is a white crystalline solid which melts at 130°C. The yield of the reaction is 90%.

Example 2 - Preparation of (N-carbamyl-N'-morpholinomethyl carbamyl)cystamine

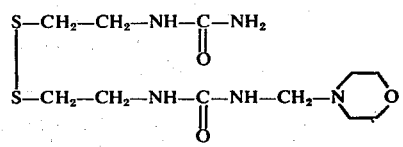

1 mol of N,N'-dicarbamyl-cystamine, 1 mol of formol in an aqueous 30% solution, 1 mol of morpholine and 50 cc of distilled water are mixed while stirring.

While the resulting reaction is exothermic, it is nevertheless necessary to heat the above mixture to 50°–55°C so as to dissolve the reagents. The mixture is then permitted to revert to ambient temperature and is then cooled to −15°C. The reaction product solidifies, and is dried under vacuum on $P_2O_5$.

It is a white crystalline product. The yield of the reaction is better than 90%.

Total amines 3.0 meq/g. Theoretical 2.96 meq/g.
Tertiary amines 2.7 meq/g. Theoretical 2.96 meq/g.

Example 3 - Preparation of N,N'-(morpholinomethylcarbamyl) cystamine.

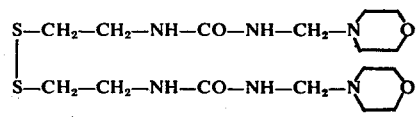

1 mol of N,N'-dicarbamyl cystamine, 2 mols of formol in an aqueous 30% solution, 2 mols of morpholine and 50 cc of distilled water are mixed together while stirring.

The resulting mixture is heated to about 55°–60°C until the reactants are completely dissolved. After cooling, the mixture is evaporated under vacuum at a temperature below 40°C. The residue is a white crystalline product. The yield of the reaction is greater than 90%.

Tertiary amines 4.0 meq/g. Theoretical 4.6 meq/g.

Example 4 - Preparation of (dimethyl-copra-morpholino-methylureido-ethyl)ammonium chloride.

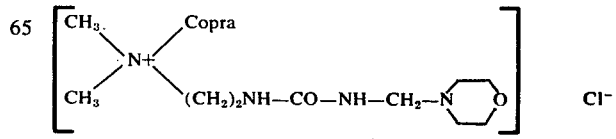

1 mol of (dimethyl, copra, ureidoethyl)ammonium chloride, prepared by quaternization of dimethyl copra with chloroethylurea, is dissolved in distilled water. 1 mol of formol in an aqueous 30% solution is then added. Morpholine is then added slowly, while stirring. The reaction is exothermic. The temperature is kept near 50°C. When the temperature falls, the reaction mixture is evaporated until dry and it is then redissolved by heating it in 2400 cc of ethanol. This mixture is then again evaporated until dry. The resulting product is a yellow oil, which after mixing with ether and vacuum drying, forms a translucent lightcolored paste. The yield of the reaction is 87%.

Example 5 - Preparation of N-methyl-di(morpholinomethyl) propylurea

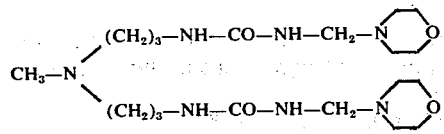

1 mol of N-methyl dipropylurea, 2 mols of formol in an aqueous 30% solution, and 2 mols of morpholine are mixed while stirring, and then heated for 30 minutes at 50°C. The reaction mixture is evaporated until dry, and after washing several times with ether and vacuum drying on $P_2O_5$, the result is a white crystalline product.

The yield of the reaction is 82.5%.
Total amines 6.57 meq/g. Theoretical 7.0 meq/g.
Tertiary amines 6.32 meq/g. Theoretical 7.0 meq/g.

Example 6 - Preparation of N-(morpholinomethyl carbamyl) cysteamine

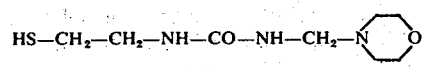

1 mol of N-carbamyl cysteamine, 1 mol of formol in an aqueous 30 % solution, 1 mol of morpholine and 10cc of distilled water are mixed while stirring. The reaction is exothermic (52°C). After cooling to about 30°C, 10cc of water is added and the mixture heated to 60°C until the reactants are completely dissolved. The mixture is then evaporated and redissolved by heating it in ethanol. This mixture is then again evaporated until dry and after washing with 50cc of ether and vacuum drying on $P_2O_5$, the result is a yellow colored paste (hygroscopic)-
The yield of the reaction is 100 %.
Total amines 4.60 meq/g. Theoretical 4,57 meq/g

Example 7 - Preparation of N-(morpholinomethylcarbamyl)glycine

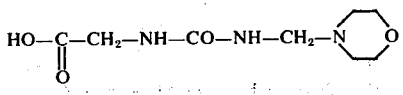

1 mol of N-carbamyl glycine and 1 mol of formol are mixed while stirring. This mixture is cooled with ice-bath and 1 mol of morpholine is added slowly while keeping the temperature at about 15°C during 30 feet and at about 50°C during the same time. After cooling the resulting mixture is evaporated until dry. The residue is a white colored paste. The yield of the reaction is 98 %.
Total amines 4.28 meq/g. Theoretical 4.60 meq/g.

Example 8 - Preparation of (diethyl methyl morpholinomethylureidoethyl)ammonium iodide

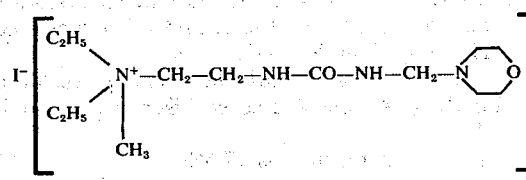

1 mol of (diethyl methyl ureidoethyl)ammonium, prepared according to the following scheme, is dissolved in distilled water.

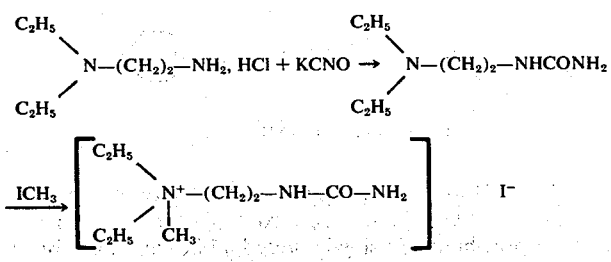

To this solution 1 mol of formol in an aqueous 30 % solution is added and then slowly and under stirring 1 mol of morpholine. The reaction is exothermic. The temperature is kept near 50°C. When the temperature falls, the reaction mixture is evaporated until dry. The resulting product is a paste. The yield of the reaction is 96 %.
Total amines 2.32 meq/g. Theoretical 2.50 meq/g.
Tertiary amines 1.96 meq/g.

Example 9 - Preparation of N-(morpholinomethyl)ethylurea diethyl ethylurea ammonium chloride

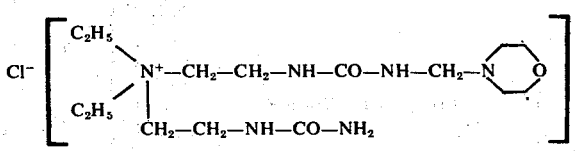

This compound is prepared according to the following scheme:

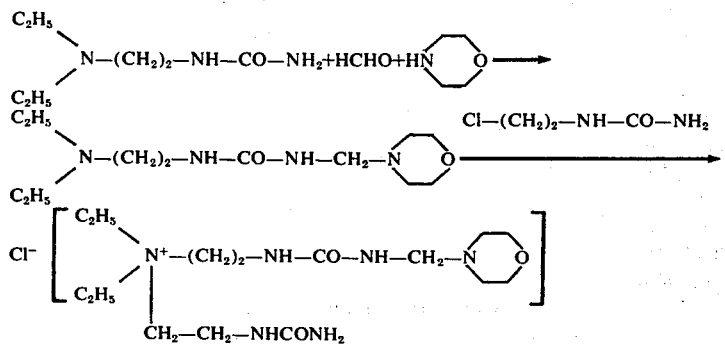

1 mol of diethyl amino ethylurea and 1 mol of formol are mixed and the reaction temperature raised from 24°C to 37°C.

To this mixture 1 mol of morpholine is then slowly added. The reaction is exothermic (50°C). The mixture is then cooled and stirred during half an hour.

To the aqueous solution ethanol and quickly chloroethylurea are added while stirring.

The resulting mixture is heated until the reactants are completely dissolved and the heating is maintained during 2h 30 to 3h at 70/80°C.

After evaporation to dryness the resulting residue is dried on $P_2O_5$. A yellow colored viscous product is obtained.

The yield of the reaction is 97,5%.
Total amines 2.63 meq/g
Theoretical 2.63 meq/g Example 10 - Preparation of N-methylpropylurea (morpholinomethyl)propylurea

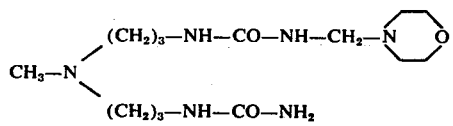

1 mol of N-methyl dipropylurea and 1 mol of formol in aqueous 30% solution are mixed. To this solution 1 mol of morpholine is slowly added while cooling. The stirring is maintained one hour after the end of the N-methyl dipropylurea addition. After evaporation to dryness a crystalline product is obtained which melts at 110°C. The yield of the reaction is 98%.
Total amines: 5.69 meq/g.
Theoretical 6.06 meq/g.
Tertiary amines: 5.80 meq/g.

Example 11 - Preparation of (N-dimethyl-ethylurea -N'-dimethylmorpholinomethylureidoethyl)cysteamine dichloride

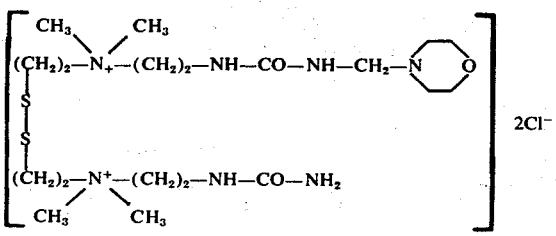

1 mol of (N-N' dimethyl N-N' ethylurea) cysteamine dichloride, obtained by quaternization of N-N' dimethyl cysteamine with 2 moles of chloroethylurea, is dissolved in distilled water.

To this solution 1 mol of formol in aqueous 30% solution and subsequently 1 mol of morpholine are added.

The reaction is exothermic (30°C). The solvent is then evaporated to dryness and a white colored paste is obtained.

The yield of the reaction is 90%.
Tertiary amines: 1.68 meq/g.
Theoretical 1.81 meq/g.

N-dodecyl, N'(morpholinomethyl)urea and N-octadecyl N'-(morpholinomethyl)urea are obtained by first preparing N-dodecyl urea and N-octadecylurea according to organic synthesis Vol. 3 - 1963 page 515 and then carrying out a Mannich reaction in the presence of 1 mol of formol and 1 mol of morpholine according to one of the preceding example.

EXAMPLES OF USE

EXAMPLE 12

A head of hair is first bleached with a conventional oxidizing composition, rinsed, and dried. The hair is then impregnated with the following solution:

| | |
|---|---|
| monomorpholinomethyl thiourea | 2 g |
| polyvinylpyrrolidone/vinyl acetate copolymer 60/40 - K value (1 % ethanol solution) 30–50 | 0.4 g |
| acetic acid, q.s.p. | pH = 2.8 |
| water, q.s.p. | 100 cc |

The hair is then set and dried under a hood for 30 to 40 minutes at a temperature of about 45-50°C. The hair is markedly hardened and is easily arranged. The tips of the hair appear to be in good condition. The set is springly, and lasts well.

EXAMPLE 13

Example 12 is repeated except that the solution contains 2 g of dimorpholinomethylurea rather than 2 g of monomorpholinomethyl thiourea and the acetic acid is replaced by sulfuric acid in amounts effective to impart a pH of 1 to said solution.

EXAMPLE 14

A solution having the following composition is applied to natural hair which has first been washed and dried:

| | |
|---|---|
| 1,4-bis(carbamidomethyl)piperazine | 4 g |
| Water | 100 cc |

The hair is then wound up on setting rollers and carefully impregnated with a 2% lactic acid solution. The hair is left to dry under a hood at about 45°C and a set of excellent quality results.

EXAMPLE 15

Example 14 is repeated except that the 1,4-bis (carbamidomethyl)piperazine is replaced by an essentially equivalent amount of dimorpholinomethylthiourea and the 2% lactic acid solution is replaced by a 2% citric acid solution.

EXAMPLE 16

Hair which has been strongly bleached is impregnated with a solution obtained by mixing, just before use, a powder containing:

| | |
|---|---|
| monomorpholinomethylurea | 6 g |
| urea | 1 g | with 100 cc of a phosphoric acid solution diluted to a pH of 2.5.

The hair is dried while keeping the temperature between 40° and 45°C for about 30 minutes.

Hair which has thus been treated is permanently waved in a conventional manner. The results of this permanent are excellent, whereas it is usually impossible to give a satisfactory permanent wave immediately after bleaching.

EXAMPLE 17

Example 16 is repeated except that the monomorpholinomethylurea is replaced with an essentially equivalent amount of monomorpholinomethylethyleneurea and the phosphoric acid is replaced with formic acid in amounts sufficient to impart to the solution a pH of 3.5.

EXAMPLE 18

The following composition is applied to hair which has just been bleached in a conventional manner.

| | |
|---|---|
| (dimethyl-copra-morpholinomethyl-ureido ethyl) ammonium chloride | 1 g |
| methyl-propylurea N-(morpholinomethyl) propylurea amine | 1 g |
| acetic acid, q.s.p. | pH = 2.5 |
| water | 100 cc |

The hair is then set in a conventional manner and excellent results are obtained with respect to resilience and holding power, as well as the condition, feel and sheen of the treated hair.

EXAMPLE 19

Example 18 is repeated except that the (dimethyl-copra-morpholinomethylureido ethyl)ammonium chloride is replaced with an essentially equivalent amount of (diethylmethyl-morpholinomethyl ureidoethyl)ammonium iodide and the acetic acid is replaced with p-toluenesulfonic acid in amounts sufficient to impart to the composition a pH of 4.

EXAMPLE 20

Example 19 is repeated except that the methyl-propylurea N-(morpholinomethyl)propylurea amine is replaced with an essentially equivalent amount of methyl-di[N-(morpholinomethyl)propylurea] amine and the acetic acid is replaced with tartaric acid in amounts sufficient to impart to the composition a pH of 4.5

EXAMPLE 21

A solution having the following composition is applied to hair which is to be strongly bleached.

| | |
|---|---|
| N,N'-(morpholinomethyl carbamyl) cystamine | 4 g |
| phosphoric acid q.s.p. | pH = 2.5 |
| water, q.s.p. | 100 cc |

The hair is then dried under a hood for about 30 minutes at a temperature of about 45°C.

Afterwards the hair is bleached with a conventional oxidizing agent. The quality of hair which has been thus bleached after being first treated in accordance with the invention is excellent, under both humid and dry conditions.

EXAMPLE 22

Example 21 is repeated except that the N,N'-(morpholinomethyl carbamyl)cystamine is replaced with an essentially equivalent amount of (N-dimethyl-ethylurea N'-dimethylmorpholinomethyl ureidoethyl)cystamine dichloride and the phosphoric acid is replaced with succinic acid in amounts sufficient to impart to the solution a pH of 5.

EXAMPLE 23

The first step of a conventional permanent wave is carried out using the following composition:

| | |
|---|---|
| N-(morpholinomethyl carbamyl)cysteamine | 1.3 g |
| N,N'-(morpholinomethyl carbamyl) cystamine | 4 g |
| monoethanolamine, q.s.p. | pH = 9.5 |
| water, q.s.p. | 100 cc |

The hair is impregnated with this solution, wound up on rollers of the usual diameter, and again saturated with this solution. It is then left for 15 minutes under a plastic cap at room temperature. The hair is then rinsed after which an aqueous solution of hydrogen peroxide at 6 volumes is applied. This solution has been brought to a pH of 1.5 by adding phosphoric acid.

The hair is then put under a hood and dried in a conventional manner. The result is a set of excellent quality which lasts well, with the hair shiny with a very soft feel.

EXAMPLE 24

Example 23 is repeated except that the N-(morpholinomethylcarbamyl)cysteamine is replaced with an essentially equivalent amount of diethylaminomethylurea and the phosphoric acid is replaced with glycolic acid.

EXAMPLE 25

Example 24 is repeated except that the N,N'-(morpholinomethyl carbamyl)cysteamine is replaced with an essentially equivalent amount of monomorpholinomethylethylenediurea, and the water is replaced with a water/ethyl alcohol 50/50 mixture.

EXAMPLE 26

Natural hair, or hair which has first been bleached, is permanently waved, using the following self-neutralizing composition:

| | |
|---|---|
| thioglycolic acid | 2 g |
| (N-carbamyl N'-morpholinomethyl carbamyl)cysteamine | 7 g |
| ammonia, q.s.p. | pH = 9.5 |
| water, q.s.p. | 100 cc | and then keeping the hair wound up on rollers of small diameter, under a cap, for about 15 minutes.

The hair is then rinsed with a 2% lactic acid solution and set in a conventional manner.

The result is a permanent which imparts excellent cosmetic properties to the hair, improving its sheen and giving it an agreeable feel.

The hair is springly and the wave lasts well when exposed to the weather.

EXAMPLE 27

Example 26 is repeated except that the (N-carbamyl N'-morpholinomethyl carbamyl)cysteamine is replaced with an essentially equivalent amount of N-(morpholinomethylcarbamyl) glycine and the water is replaced with a water/isopropyl alcohol 60/40 mixture.

EXAMPLE 28

Example 12 is repeated except that the monomorpholinomethyl thiourea is replaced with an essentially equivalent amount of dimorpholinomethylene diurea and the acetic acid is replaced by salicylic acid.

EXAMPLE 29

Example 12 is repeated except that the monomorpholinomethyl thiourea is replaced with an essentially equivalent amount of piperidinomethylurea and the acetic acid is replaced by oxalic acid.

EXAMPLE 30

Example 18 is repeated except that the (dimethyl-copra-morpholinomethyl-ureido ethyl)ammonium chloride is replaced with an essentially equivalent amount of [N-(morpholinomethyl)ethylurea, diethyl, ethylurea]ammonium chloride and the acetic acid is replaced by malic acid.

EXAMPLE 31

Example 21 is repeated except that the N,N'-(morpholinomethyl carbamyl)cystamine is replaced with an essentially equivalent amount of N-dodecyl, N'-(morpholinomethyl)urea and the phosphoric acid is replaced by phenylacetic acid in amounts sufficient to impart to the solution a pH of 1.0.

EXAMPLE 32

Example 21 is repeated again except that the N,N'-(morpholinomethyl carbamyl)cystamine is replaced with an essentially equivalent amount of N-octadecyl N'-(morpholinomethyl)urea and the phosphoric acid is replaced by nicotinic acid in amounts sufficient to impart to the solution a pH of 4.0.

EXAMPLE 33

Example 14 is repeated except that the 1,4-bis (carbamidomethyl)piperazine is replaced with an essentially equivalent amount of morpholinomethylurea quaternized with methyl iodide, and the water is replaced with a water/ethyl alcohol 70/30 mixture.

EXAMPLE 34

Example 16 is repeated except that the monomorpholinomethylurea is replaced with an essentially equivalent amount of methoxymethylureidomethyl pyridinium chloride and the phosphoric acid is replaced by hydrochloric acid.

What is claimed is:

1. A compound of the formula

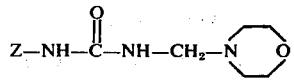

wherein Z is selected from the group consisting of

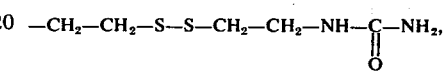

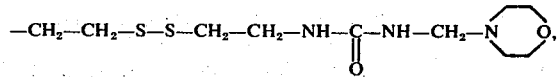

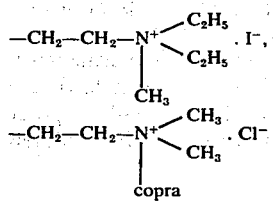

wherein copra represents a mixture of alkyl and alkenyl radicals having 6 – 18 carbon atoms,

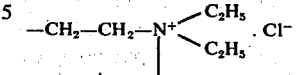

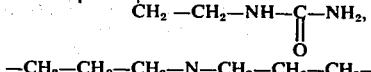

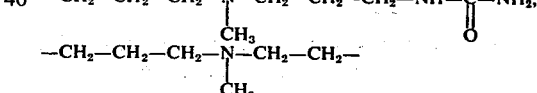

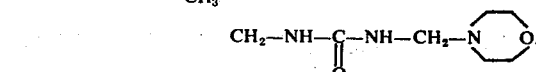

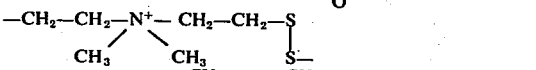

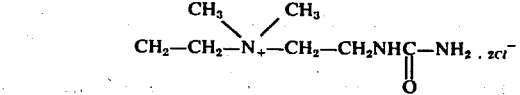

—$C_{12}H_{25}$,
and —$C_{18}H_{37}$.

2. A compound according to claim 1 which is selected from the group consisting of (N-carbamyl-N'-morpholinomethyl-carbamyl)-cystamine; N,N'-(morpholinomethyl-carbamyl) cystamine; (diethyl-methyl-morpholino-methyl ureidoethyl) ammonium iodide; (dimethyl-copra-morpholino-methyl ureidoethyl) ammonium chloride; N-(morpholinomethyl) ethylurea-diethyl-ethylurea ammonium chloride; methyl-propylurea N-(morpholinomethyl)propylurea amine; methyl-di-N-(morpholinomethyl)propylurea amine; (N-dimethyl-ethylurea-N'-dimethyl-morpholinomethyl ureidoethyl)cystamine dichloride; N-dodecyl-N'-(morpholinomethyl)urea; and N-octadecyl N'-(morpholinomethyl) urea.

* * * * *

UNITED STATES PATENT OFFICE
CERTIFICATE OF CORRECTION

Patent No. 3,957,774                    Dated May 18, 1976

Inventor(s) Gregoire Kalopissis, et al         Page 1 of 3

It is certified that error appears in the above-identified patent and that said Letters Patent are hereby corrected as shown below:

In the Heading

Add the following:

[30] Foreign Application Priority Data

October 26, 1967 Luxemburg 54,745

In the Abstract

Line 4, the structural formula should read:

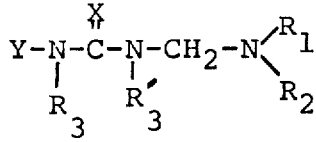

Lines 6 and 7, the structural formula should read:

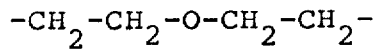

In the Specification

Column 2, lines 44-46, the structural formulas should read:

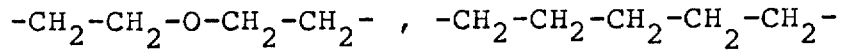

UNITED STATES PATENT OFFICE
CERTIFICATE OF CORRECTION

Patent No. 3,957,774　　　　　　　　Dated May 18, 1976

Inventor(s) Gregoire Kalopissis, et al　　Page 2 of 3

It is certified that error appears in the above-identified patent and that said Letters Patent are hereby corrected as shown below:

Column 3, line 36, the structural formula should read:

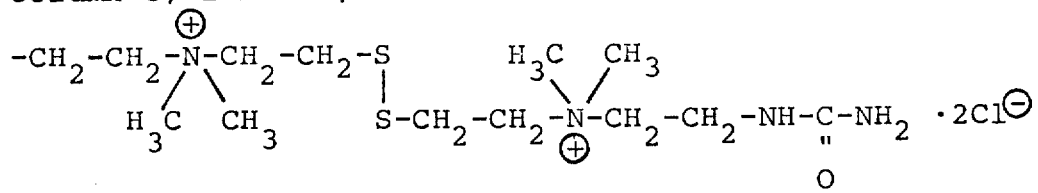

Column 4, lines 47-48, the structural formula should read:

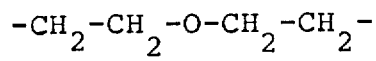

Column 7, line 1, the structural formula should read:

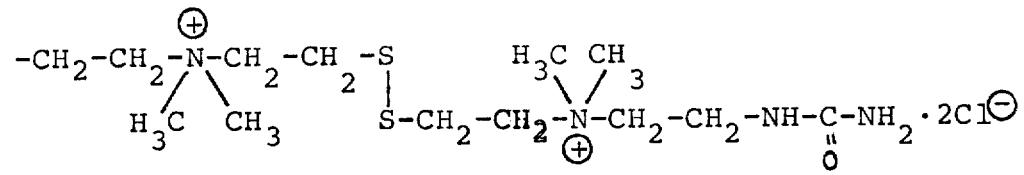

UNITED STATES PATENT OFFICE
CERTIFICATE OF CORRECTION

Patent No. 3,957,774            Dated May 18, 1976

Inventor(s) Gregoire Kalopissis, et al    Page 3 of 3

It is certified that error appears in the above-identified patent and that said Letters Patent are hereby corrected as shown below:

In the Claims

Column 16, lines 41-45, the structural formula should read:

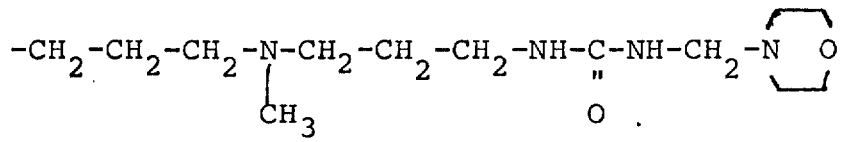

lines 46-50, the structural formula should read:

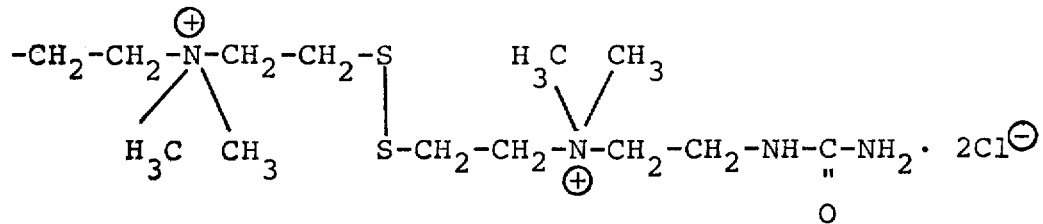

Signed and Sealed this

Twenty-first Day of September 1976

[SEAL]

Attest:

RUTH C. MASON
*Attesting Officer*

C. MARSHALL DANN
*Commissioner of Patents and Trademarks*